US012799471B2

(12) United States Patent
Wang et al.

(10) Patent No.: US 12,799,471 B2
(45) Date of Patent: Nov. 17, 2026

(54) MUTANTS OF IMMUNOGLOBULIN-DEGRADING ENZYME IDEE

(71) Applicant: SHANGHAI BAO PHARMACEUTICALS CO., LTD., Shanghai (CN)

(72) Inventors: Zheng Wang, Shanghai (CN); Yunxia Xu, Shanghai (CN); Leilei Zheng, Shanghai (CN)

(73) Assignee: Shanghai Bao Pharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 19/293,034

(22) Filed: Aug. 7, 2025

(65) Prior Publication Data

US 2025/0361498 A1 Nov. 27, 2025

Related U.S. Application Data

(63) Continuation of application No. PCT/CN2024/130963, filed on Nov. 8, 2024.

(30) Foreign Application Priority Data

Nov. 13, 2023 (CN) ......................... 202311508868.8

(51) Int. Cl.
*C12N 9/64* (2006.01)
*A61K 38/00* (2006.01)
*A61K 48/00* (2006.01)

(52) U.S. Cl.
CPC ........ *C12N 9/6472* (2013.01); *A61K 48/0016* (2013.01); *A61K 38/00* (2013.01); *C07K 2319/30* (2013.01)

(58) Field of Classification Search
CPC .. C12N 9/6472; A61K 48/0016; A61K 38/00; C07K 2319/30
See application file for complete search history.

(56) References Cited

U.S. PATENT DOCUMENTS

2023/0364207 A1* 11/2023 Liu ......................... C12N 9/54

FOREIGN PATENT DOCUMENTS

| | | | |
|---|---|---|---|
| CN | 113564150 | A | 10/2021 |
| CN | 118497176 | A | 8/2024 |
| WO | 2021254479 | A1 | 12/2021 |
| WO | 2022057942 | A1 | 3/2022 |
| WO | 2023116817 | A1 | 6/2023 |

OTHER PUBLICATIONS

Siloto R et al. Site saturation mutagenesis: Methods and Applications in protein engineering. 2012. Biocatalysis and Agricultural Biotechnology. 1:181-189. (Year: 2012).*

Jonas Lannergard, et al., IdeE, an IgG-endopeptidase of *Streptococcus equi* ssp.equi, FEMS Microbiol Lett, 2006, pp. 230-235, vol. 262.

Mark A. Batzer, et al., Enhanced evolutionary PCR using oligonucleotides with inosine at the 3'-terminus, Nucleic Acids Research, 1991, p. 5081, vol. 19, No. 18.

Eiko Ohtsuka, et al., An Alternative Approach to Deoxyoligonucleotides as Hybridization Probes by Insertion of Deoxyinosine at Ambiguous Codon Positions, The Journal of Biological Chemistry, 1985, pp. 2605-2608, vol. 260 No. 5.

Sharon Cassol, et al., Stability of Dried Blood Spot Specimens for Detection of Human Immunodeficiency Virus DNA by Polymerase Chain Reaction, Journal of Clinical Microbiology, 1992, pp. 3039-3042, vol. 30 No. 12.

Gian Maria Rossolini, et al., Use of deoxyinosine-containing primers vs degenerate primers for polymerase chain reaction based on ambiguous sequence information, Molecular and Cellular Probes, 1994, pp. 91-98, vol. 8.

STN. 18-315-Proteinase IdeE [18-methionine, 97-aspartic acid] [*Streptococcus equi equi*], STN, RN: 3004804-10-5.

Zhou Si-Han, et al., Expression, purification, and functional identification of immunoglobulin degrading enzyme IdeS in *Escherichia coli*, Acta Pharmaceutica Sinica, 2022, pp. 2234-2239, vol. 57 No. 7.

* cited by examiner

*Primary Examiner* — Paul J Holland
(74) *Attorney, Agent, or Firm* — Hoxie & Associates LLC

(57) ABSTRACT

Provided are a coding sequence of an immunoglobulin-degrading enzyme and a polypeptide encoded thereby. The function of the polypeptide at least includes the function of the immunoglobulin-degrading enzyme IdeE. The immunoglobulin-degrading enzyme includes the amino acid sequence set forth in SEQ ID NO: 2, and does not cause bacterial, fungal, or cellular autolysis during expression.

19 Claims, 4 Drawing Sheets

Specification includes a Sequence Listing.

1: Bacterial cell post-induced cultivation
2: Supernatant post-induced cultivation 1: Bacterial cell post-induced cultivation
2: Bacterial cell post-induced cultivation (debris pellet)
3: Bacterial cell post-induced cultivation (lysate supernatant)

A: Expression results of IdeE-1 expression strain in supernatant in 5-L fermenter B: Expression results of IdeE-2 expression strain in cell debris pellet in 5-L fermenter 1: Induction 0 h, 2: Induction 2 h, 3: Induction 4 h, 4: Induction 6 h, 5: Induction 8 h

SEQUENCE LISTING

```
Sequence total quantity: 3
SEQ ID NO: 1           moltype = AA  length = 297
FEATURE                Location/Qualifiers
source                 1..297
                       mol_type = protein
                       organism = synthetic construct
SEQUENCE: 1
ITSVWTKGVT PLTPEQFRYN NEDVIHAPYL AHQGWYDITK AFDGKDNLLC GAATAGNMLH  60
WWFDQNKTEI EAYLSKHPDK QKIIFNNQEL FDLKAAIDTK DSQTNSQLFN YFRDKAFPNL  120
SARQLGVMPD LVLDMFINGY YLNVFKTQST DVNRPYQDKD KRGGIFDAVF TRGDQTTLLT  180
ARHDLKNKGL NDISTIIKQE LTEGRALALS HTYANVSISH VINLWGADFN AEGNLEAIYV  240
TDSDANASIG MKKYFVGINA HGHVAISAKK IEGENIGAQV LGLFTLSSGK DIWQKLS     297

SEQ ID NO: 2           moltype = AA  length = 298
FEATURE                Location/Qualifiers
source                 1..298
                       mol_type = protein
                       organism = synthetic construct
SEQUENCE: 2
MITSVWTKGV TPLTPEQFRY NNEDVIHAPY LAHQGWYDIT KAFDGKDNLL CGAATAGNML  60
HWWFDQNKTE IEAYLSKHPD KQKIIFNNQE LFDLKAAIDT KDSQTNSQLF NYFRDKAFPN  120
LSARQLGVMP DLVLDMFING YYLNVFKTQS TDVNRPYQDK DKRGGIFDAV FTRGDQTTLL  180
TARHDLKNKG LNDISTIIKQ ELTEGRALAL SHTYANVSIS HVINLWGADF NAEGNLEAIY  240
VTDSDANASI GMKKYFVGIN AHGHVAISAK KIEGENIGAQ VLGLFTLSSG KDIWQKLS    298

SEQ ID NO: 3           moltype = DNA  length = 900
FEATURE                Location/Qualifiers
source                 1..900
                       mol_type = other DNA
                       organism = synthetic construct
SEQUENCE: 3
atgatcacca gcgtgtggac caaaggtgtt accccgctga ccccggagca gttccgttac  60
aacaacgaag acgttattca cgcgccgtac ctggcgcacc aaggttggta tgatatcacc  120
aaggcgttcg acggcaaaga taacctgctg tgcggtgcgg cgaccgcggg taacatgctg  180
cactggtggt ttgaccagaa caagaccgag attgaagcgt acctgagcaa acacccggat  240
aagcagaaga tcatcttcaa caaccaagaa ctgttcgacc tgaaggcggc gatcgacacc  300
aaagatagcc agaccaacag ccaactgttc aactattttc gtgataaggc gtttccgaac  360
ctgagcgcgc gtcagctggg tgtgatgccg gacctggttc tggatatgtt cattaacggc  420
tactatctga acgtgtttaa aacccagagc accgatgtta accgtccgta ccaagacaag  480
gataaacgtg gtggcatctt cgacgcggtg tttacccgtg gtgatcagac caccctgctg  540
accgcgcgtc acgacctgaa gaacaaaggt ctgaacgata ttagcaccat cattaagcaa  600
gaactgaccg aaggtcgtgc gctggcgctg agccacacct atgcgaacgt gagcatcagc  660
cacgttatta acctgtgggg tgcggacttc aacgcggagg gcaacctgga agcgatctac  720
```

-continued

```
gtgaccgaca gcgatgcgaa cgcgagcatt ggcatgaaga aatattttgt gggtatcaac  780
gcgcacggcc acgttgcgat cagcgcgaag aaaattgagg gtgaaaacat cggcgcgcag  840
gttctgggtc tgttcaccct gagcagcggc aaggatattt ggcaaaaact gagctaatga  900
```

MUTANTS OF IMMUNOGLOBULIN-DEGRADING ENZYME IDEE

CROSS REFERENCE TO THE RELATED APPLICATIONS

This application is a continuation application of International Application No. PCT/CN2024/130963, filed on Nov. 8, 2024, which is based upon and claims priority to Chinese Patent Application No. 202311508868.8 filed on Nov. 13, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBSRWA025-track-one_Sequence_Listing.xml, created on Jul. 28, 2025, and is 5,021 bytes in size.

TECHNICAL FIELD

The present disclosure relates to the field of biotechnology, and in particular to mutants of an immunoglobulin-degrading enzyme and expression thereof.

BACKGROUND

Immunoglobulin G (IgG) is the main antibody component in serum, and accounts for about 75% of serum immunoglobulins. It mainly serves a protective function in immune defense by effectively preventing infectious diseases. Beyond its protective role, IgG exhibits disease associations. In some autoimmune diseases, IgG antibodies react with self-antigens, and IgG can induce acute transplant rejection in organ transplantation.

Immunoglobulin G-degrading enzyme of *Streptococcus pyogenes* (IdeS) is an extracellular cysteine protease produced by the human pathogen *S. pyogenes*. IdeS catalyzes a single proteolytic cleavage in the lower hinge region of the heavy chain across all human IgG subclasses. IdeS efficiently cleaves IgG into Fc and $F(ab')_2$ fragments through a two-stage enzymatic mechanism. In the first stage, one (first) IgG heavy chain is cleaved to produce a single-cleaved IgG (scIgG) molecule with a non-covalently bound Fc molecule. The scIgG molecule is an intermediate product that retains the remaining (second) heavy chain of the original IgG molecule. In the second stage, the second heavy chain is cleaved by IdeS to release a $F(ab')_2$ fragment and a homodimeric Fc fragment, which facilitate Group A *Streptococcus* (GAS) evasion of antibody-mediated phagocytosis and cellular responses, thereby attenuating host immune clearance of GAS pathogens. IdeE is derived from *Streptococcus equi ssp. equi*, an equine pathogen (Jonas Lannergård, Bengt Guss, *FEMS Microbiol Lett.,* 2006, 262:230-235). The two enzymes, IdeE and IdeS, cleave IgG at exactly the same position. The cleavages are highly reproducible and specific, and have a very similar substrate range.

Given the applications of the immunoglobulin-cleaving enzymes described above, there is substantial demand for immunoglobulin-degrading enzymes and the large-scale production thereof.

SUMMARY

In some aspects of the present disclosure, provided is an immunoglobulin-degrading enzyme that reduces or eliminates bacterial, fungal, or cellular autolysis during induced expression. In some embodiments, the immunoglobulin-degrading enzyme of the present disclosure does not cause bacterial, fungal, or cellular autolysis.

In some embodiments, during expression of the immunoglobulin-degrading enzyme of the present disclosure, $OD_{600}$ value of the bacteria, fungi, or cells does not decrease after exceeding 40, 50, 60, 70, or 80; preferably, during expression of the immunoglobulin-degrading enzyme, $OD_{600}$ value of the bacteria, fungi, or cells does not decrease after exceeding 70; more preferably, during expression of the immunoglobulin-degrading enzyme, $OD_{600}$ value of the bacteria, fungi, or cells does not decrease after exceeding 80.

In some embodiments, during expression of the immunoglobulin-degrading enzyme of the present disclosure (e.g., 4 h, 8 h, 12 h, 16 h, 24 h, or longer following induced expression), $OD_{600}$ value of the bacteria does not decrease after exceeding 40, 50, 60, 70, or 80.

In some aspects of the present disclosure, provided is an immunoglobulin-degrading enzyme, which comprises or consists of:

(a) an amino acid sequence set forth in SEQ ID NO: 2; or (b) an amino acid sequence having one or more amino acid substitutions, additions, and/or deletions compared with SEQ ID NO: 2.

In some embodiments, the immunoglobulin-degrading enzyme of the present disclosure comprises or consists of the amino acid sequence set forth in SEQ ID NO: 2.

In some embodiments, the immunoglobulin-degrading enzyme comprises or consists of the amino acid sequence set forth in SEQ ID NO: 2, wherein the encoding sequence reduces or eliminates bacterial, fungal, or cellular autolysis during expression. In some embodiments, the immunoglobulin-degrading enzyme does not cause bacterial, fungal, or cellular autolysis during induced expression.

In some embodiments, the immunoglobulin-degrading enzyme of the present disclosure is derived from *Streptococcus equi ssp. equi.*

In some embodiments, the immunoglobulin-degrading enzyme of the present disclosure is intracellularly expressed or extracellularly expressed.

In some aspects of the present disclosure, provided is a nucleotide sequence encoding the immunoglobulin-degrading enzyme of the present disclosure. In some embodiments, the nucleotide sequence encoding the immunoglobulin-degrading enzyme of the present disclosure comprises or consists of:

(a) a nucleotide sequence set forth in SEQ ID NO: 3; or (b) a nucleotide sequence having at least 85%, at least 90%, at least 95%, at least 96%, at least 97%, at least 98%, at least 99%, but less than 100% sequence homology to the nucleotide sequence set forth in SEQ ID NO: 3;

(c) a nucleotide sequence having one or more nucleotide substitutions, additions, and/or deletions compared with SEQ ID NO: 3.

In some aspects of the present disclosure, provided is an expression vector, which comprises the nucleotide sequence of the present disclosure.

In some aspects of the present disclosure, provided is a host cell, which comprises the nucleotide sequence of the present disclosure or the expression vector of the present disclosure. In some embodiments, the host cell of the present disclosure is a bacterial cell or a fungal cell. In some embodiments, the host cell of the present disclosure is an *Escherichia coli* cell or a yeast cell.

In some aspects of the present disclosure, provided is a method for intracellular expression of the immunoglobulin-degrading enzyme of the present disclosure, which comprises the following steps:

(a) selecting a single colony of the host cell of the present disclosure;
(b) culturing a seed culture;
(c) culturing the seed culture in a fermenter;
(d) inducing expression of the immunoglobulin-degrading enzyme; and
(e) optionally collecting the expressed immunoglobulin-degrading enzyme.

In some aspects of the present disclosure, provided is a composition, which comprises the immunoglobulin-degrading enzyme of the present disclosure; and optionally a pharmaceutically acceptable carrier or excipient.

In some embodiments, the composition of the present disclosure further comprises: an antibody or a protein comprising an Fc fragment, wherein a target of the antibody is preferably selected from the following group: a cell surface protein, a cytokine, a hormone, an enzyme, an intracellular messenger, an intercellular messenger, and an immune checkpoint inhibitor. In some embodiments, the composition of the present disclosure further comprises: a viral vector drug or a drug capable of reducing a blood IgG level, wherein the viral vector drug is selected from the following group: an oncolytic virus, a gene therapy virus, and a viral vector vaccine. The drug capable of reducing the blood IgG level is selected from the following group: an FcRn antibody and an Fc fragment variant with high affinity for FcRn.

In some aspects of the present disclosure, provided is a kit, which includes:

(1) the immunoglobulin-degrading enzyme of the present disclosure; and
(2) one or more selected from the following group: (a) a pharmaceutically acceptable carrier or excipient; (b) an antibody or a protein comprising an Fc fragment; and/or
(3) a viral vector drug selected from an oncolytic virus, a gene therapy virus, and a viral vector vaccine; and/or
(4) a drug capable of reducing a blood IgG level selected from an FcRn antibody and an Fc fragment variant with high affinity for FcRn.

In some embodiments, the kit of the present disclosure includes a kit A (the first kit) and a kit B (the second kit), where the kit A includes the immunoglobulin-degrading enzyme of the present disclosure, and the kit B includes one or more selected from the following group: (1) a pharmaceutically acceptable carrier or excipient; (2) an antibody or a protein comprising Fc; and/or (3) a viral vector drug; and/or (4) a drug capable of reducing a blood IgG level. In some embodiments, the viral vector drug is selected from the following group: an oncolytic virus, a gene therapy virus, and a viral vector vaccine. In some embodiments, the drug capable of reducing the blood IgG level is selected from the following group: an FcRn antibody and an Fc fragment variant with high affinity for FcRn.

DETAILED DESCRIPTION OF THE EMBODIMENTS

Figure 1:
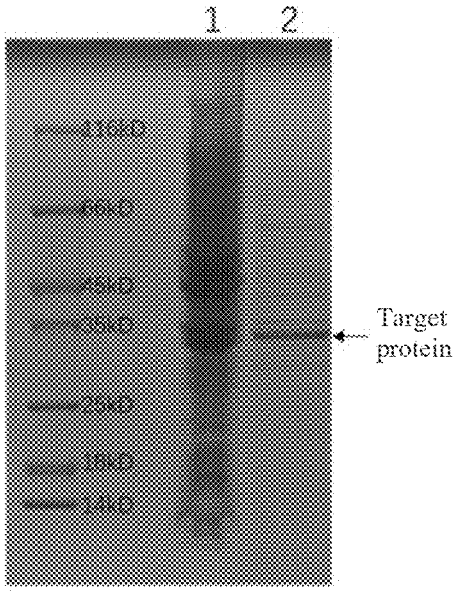
FIG. 1 shows the electrophoretic results of the expressed products in the shake-flask fermentation supernatant of the IdeE-1 expression strain.

I. Functional Polypeptide Having Immunoglobulin-Degrading Enzymatic Activity In a first aspect of the present disclosure, provided is a functional polypeptide. The functional polypeptide has immunoglobulin-degrading enzymatic activity and comprises the amino acid sequence set forth in SEQ ID NO: 2.

In some embodiments, the polypeptide of the present disclosure is produced by genetic engineering recombination.

In some embodiments, the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the sequence set forth in SEQ ID NO: 2. In some embodiments, the polypeptide has one or more amino acid substitutions, insertions, and/or deletions compared with SEQ ID NO: 2.

In some embodiments, the coding sequence of the polypeptide is set forth in SEQ ID NO: 3, or has at least 80%, at least 85%, at least 90%, at least 91%, at least 92%, at least 93%, at least 94%, at least 95%, at least 96%, at least 97%, at least 98%, or at least 99% sequence identity to the nucleotide sequence set forth in SEQ ID NO: 3. The coding sequence does not cause bacterial, fungal, or cellular autolysis during expression. In some embodiments, the coding sequence of the polypeptide has one or more nucleotide substitutions, insertions, and/or deletions compared with SEQ ID NO: 3.

II. Preparation of Functional Polypeptide Having Immunoglobulin-Degrading Enzymatic Activity In a second aspect of the present disclosure, provided is a nucleotide encoding the polypeptide or mutant.c Additionally, in the present disclosure, further provided is a vector comprising a nucleic acid molecule encoding the polypeptide or mutant. The vector may further comprise an expression control sequence operably linked to the sequence of the nucleic acid molecule to facilitate expression of the protein or mutant.

Various suitable nucleic acid molecules encoding the polypeptide or mutant described above are suitable for use in the present disclosure. The sequences mentioned in the examples below are suitable for use in the method of the present disclosure. It should be understood that upon provision of an amino acid sequence of a protein or polypeptide, those skilled in the art can readily determine a nucleic acid molecule encoding the protein or polypeptide.

Various suitable vectors can be used, such as those for use in cloning and expression in mammals, bacteria, fungi, or yeast, including pET and those described in the *Cloning Vectors: A Laboratory Manual* (Pouwels et al., latest edition by Elsevier). In some embodiments of the present disclosure, the vector is a vector suitable for use in *Escherichia coli* cells.

In some embodiments, the vector may be a viral vector, such as, but not limited to, a retroviral vector, a phage vector, an adenoviral vector, a herpes simplex virus (HSV) vector, an adeno-associated virus (AAV) vector, or a lentiviral vector.

The expression vector comprises a DNA sequence of the protein or mutant linked to an appropriate transcriptional and translational regulatory sequence derived from a mammalian, microbial, viral, or insect gene. The regulatory sequence comprises a transcriptional promoter, an operator, an enhancer, a ribosome binding site, or an appropriate sequence controlling the initiation and termination of transcription and translation. When regulation of sequence functionality is required for the polypeptide or mutant described above, an appropriate regulatory sequence is linked thereto. For example, the promoter sequence is positioned upstream of the DNA sequence encoding the protein or mutant. The replication ability within host cells is usually regulated by an origin of replication. A selectable marker gene for identifying transformed strains may also be added to the expression vector.

Additionally, a leader sequence can be fused to the coding sequence of the polypeptide or mutant, enabling extracellular secretion of the translated protein or mutant. A signal peptide can enhance the extracellular secretion of the chimeric polypeptide from the host cell. The signal peptide may be cleaved off during the secretion of the polypeptide from the cell.

In the present disclosure, further provided is an expression system (e.g., a host cell) for expressing the polypeptide or mutant described above. The system comprises the expression vector of the present disclosure or has an exogenous polynucleotide of the present disclosure integrated into its genome. Any cell suitable for expression using an expression vector can serve as a host cell. For example, the host cell may be selected from a prokaryotic cell (e.g., a bacterial cell); a lower eukaryotic cell (e.g., a yeast cell); a higher eukaryotic cell (e.g., a mammalian cell), and the like. The host cell may be selected from, but not limited to, a bacterial cell (e.g., *Escherichia coli, Streptomyces* spp., and *Salmonella typhimurium*); a fungal cell (e.g., yeast, filamentous fungi, and a plant cell); an insect cell (e.g., *Drosophila* S2 or Sf9); an animal cell(e.g., CHO, COS, an HEK293 cell, and a Bowes melanoma cell), and the like. The host cell may be one or a combination of two or more cells selected from the aforementioned groups. Methods for constructing the expression system may be known to those skilled in the art and may be, for example, one or a combination of two or more methods including, but not limited to, chemical transformation, microinjection, biolistics, electroporation, viral-mediated transduction, electron bombardment, calcium phosphate precipitation, and the like. As an exemplary mode of the present disclosure, the expression system is a prokaryotic expression system, such as an *Escherichia coli* expression system and a *Bacillus subtilis* expression system. In more specific embodiments, the *Escherichia coli* cell is BL21, BL21 (DE3), BL21 (DE3) pLysS, BL21 (DE3) pLysE, BL21 Star (DE3), BL21 Star (DE3) pLysS, Lemo21 (DE3), T7 Express lysY, T7 Express lysY/Iq, SHuffle, Origami, Rosetta, HMS174, or the like.

A method for producing the polypeptide or mutant described above is also encompassed by the present disclosure. The method includes culturing a recombinant cell comprising a nucleic acid molecule encoding the polypeptide or mutant protein described above. The method may include allowing the cell to express the encoded polypeptide or mutant described above and allowing renaturation of the expressed polypeptide or mutant protein described above. The product of the method is also protected.

Steps for the intracellular or extracellular expression include: selection of single colonies of an expression strain, preparation of a seed culture, scale-up cultivation in a fermenter, induction of protein expression, and sample collection at the termination of fermentation.

Further, the steps for the intracellular expression include: inoculating a production strain on an agar plate, picking a single colony and inoculating the same into a test tube/shake-flask containing a culture medium, continuing cultivation with or without transfer into a larger-volume shake-flask/fermenter, transferring the cultured bacterial culture into a fermenter with a certain volume for culturing, adding an inducer or applying other induction methods, continuing cultivation until fermentation completion, and collecting the culture.

Further, the steps for the intracellular expression described in the embodiments of the present disclosure include: inoculating a production strain on an LB agar plate containing 100 μg/mL ampicillin; incubating at 37° C. overnight until colonies grew out; picking a single colony and inoculating the same into 3 mL of an LB medium containing 100 μg/mL ampicillin, followed by culturing at 37° C. and 250 rpm overnight; inoculating 500 μL of the overnight bacterial culture into 50 mL of an LB medium containing 100 μg/mL ampicillin, culturing at 37° C. for 2-4 h, adding 0.1 mM IPTG for induction, and continuing induced cultivation overnight; or inoculating a production strain on an LB agar plate containing 100 μg/mL ampicillin; incubating at 37° C. overnight until colonies grew out; picking a single colony and inoculating the same into 3 mL of an LB medium containing 100 μg/mL ampicillin, followed by culturing at 37° C. and 250 rpm overnight; inoculating 500 μL of the overnight bacterial culture into 50 mL of an LB medium containing 100 μg/mL ampicillin, culturing overnight, inoculating 2.5 mL of the resulting culture into 250 mL of a medium, incubating at 37° C. overnight, and transferring to a 5-L fermenter for fermentation cultivation using fed-batch and deep aeration methods. Glycerol or glucose is selected as the limiting carbon source for pre-induction control of feeding, and IPTG and lactose are respectively selected as the inducer and the limiting carbon source for post-induction control of feeding. The fermentation is performed at 37° C., and pH is controlled at 6.0-7.2 by adding 25% ammonium hydroxide. The aeration rate of the fermenter is set to 0.5-2.0 vvm, and dissolved oxygen is maintained at about 30% by controlling the feeding rate, stirring speed, and aeration rate. During the fermentation, samples are periodically taken to measure $OD_{600}$, and when $OD_{600}$ reaches a predetermined value, IPTG/lactose feeding is initiated for induction. Fermentation is terminated after 8-16 h of induced cultivation.

III. Pharmaceutical Combination

In a third aspect of the present disclosure, provided is a composition, which comprises the polypeptide or mutant described above or a protein comprising the polypeptide or mutant thereof described above, and optionally a pharmaceutically acceptable carrier or excipient.

3.1 Target of Antibody

In some embodiments, the composition described above comprises an antibody. A target of the antibody may be selected from a cell surface protein, a cytokine, a hormone, an enzyme, an intracellular messenger, an intercellular messenger, an immune checkpoint, or the like, or any combination thereof.

3.2 Targeted Drug

In some embodiments, the composition further comprises a targeted drug, a chemotherapeutic drug, or an immune checkpoint inhibitor.

3.3 Drug Capable of Reducing Blood IgG Level

In some embodiments, the composition described above comprises a polypeptide drug capable of reducing the blood IgG level. The polypeptide drug is capable of blocking the binding of blood IgG to the FcRn protein.

3.4 Viral Vector Drug

In some embodiments, the composition described above comprises a viral vector drug. A virus used in the viral vector drug is selected from an ssDNA virus, a dsDNA virus, an ssRNA virus, and a dsRNA virus; and/or the virus used in the viral vector drug is selected from a wild-type virus strain or naturally attenuated strain, a genetically engineered and selectively attenuated strain, a gene-loaded virus strain, and a gene transcription-targeted virus strain.

3.5 Gene Therapy Drug

In some embodiments, the composition described above comprises a gene therapy virus. The gene therapy virus expresses an exogenous gene, and the exogenous gene encodes a protein required for a gene defective disease.

IV. Product

In the present disclosure, further provided is a product, which comprises the mutant or protein described above and a therapeutic agent; the therapeutic agent is selected from a viral vector drug, an antibody, and a polypeptide drug capable of reducing the blood IgG level.

In the present disclosure, further provided is a kit or kit of parts. The kit includes: 1) a therapeutically effective amount of a drug comprising the mutant described above; and 2) a therapeutically effective amount of a therapeutic agent selected from a viral vector drug, an antibody, and a polypeptide drug capable of reducing the blood IgG level. In some embodiments, the viral vector drug is an oncolytic virus or a gene therapy virus. The kit can further include 3) a targeted drug or a chemotherapeutic drug or an immune checkpoint inhibitor.

The kit or kit of parts includes a kit A and a kit B. The kit A includes a therapeutically effective amount of the mutant or protein described above, and the kit B includes a therapeutically effective amount of a therapeutic agent selected from a viral vector drug, an antibody, and a polypeptide drug capable of reducing the blood IgG level.

The kit can include instructions on the administration of the therapeutically effective amount of the mutant or protein described above and the therapeutically effective amount of the therapeutic agent (e.g., dose information and administration interval information). The therapeutic agent is selected from a viral vector drug, an antibody, and a polypeptide drug capable of reducing the blood IgG level.

The pharmaceutical carrier can be liquid, and the pharmaceutical composition can be in the form of a solution. Liquid carriers are used to prepare solutions, suspensions, emulsions, syrups, elixirs, and pressurized compositions. The active ingredients can be dissolved or suspended in a pharmaceutically acceptable liquid carrier, such as water, an organic solvent, a mixture of the two, or a pharmaceutically acceptable oil or fat.

The pharmaceutical composition for parenteral administration is sterile, substantially isotonic, and pyrogen-free, and is prepared in accordance with the GMP of the FDA or a similar agency. The viral vector drug can be administered as an injectable dosage form of a solution or suspension thereof, where the substance is in a physiologically acceptable diluent and pharmaceutical carrier (which can be a sterile liquid, such as water, oil, saline, glycerol, or ethanol). In addition, an auxiliary substance such as a wetting agent or an emulsifier, a surfactant, and a pH buffering substance can be present in the composition. Other components of the pharmaceutical composition include petroleum, and/or components from animal, plant, or synthetic origin, such as peanut oil, soybean oil, and mineral oil. In general, diols such as propylene glycol or polyethylene glycol are preferred liquid carriers, especially for injectable solutions. The viral vector drug can be administered in the form of a depot injection or an implanted preparation, which can be formulated to allow sustained release of the active ingredient. Typically, the composition is prepared as an injectable preparation, i.e., a liquid solution or suspension, or can be prepared as a solid form suitable for dissolution or suspension in a liquid carrier prior to injection.

Unless otherwise defined, all technical and scientific terms used herein have the same meanings as commonly understood by those of ordinary skill in the art to which the present disclosure belongs. While any methods, devices, and materials similar or equivalent to those described herein can be used in the practice or testing of the present disclosure, preferred methods, devices, and materials are now described.

As used herein, the term "immunoglobulin-degrading enzyme" refers to any enzyme or a functional fragment thereof that hydrolytically cleaves in the lower hinge region of the heavy chain of a substrate immunoglobulin, effectively cleaving IgG into Fc and $F(ab')_2$ fragments. The term "immunoglobulin-degrading enzyme" includes a variant having one or more amino acid substitutions, deletions, or insertions relative to the sequence of the immunoglobulin-degrading enzyme of SEQ ID NO: 2, and/or a fusion protein or conjugate comprising sialidase. The immunoglobulin-degrading enzyme is also referred to as an IgG-degrading enzyme, and unless otherwise specified, these two terms are used interchangeably herein. As used herein, the term "having immunoglobulin-degrading enzymatic activity" means that the polypeptide retains, for example, at least 10%, at least 20%, at least 30%, at least 40%, at least 50%, at least 60%, at least 70%, at least 80%, at least 90%, or 100% of its enzymatic activity.

The term "nucleotide" or "polynucleotide" means a single-stranded or double-stranded deoxyribonucleotide, deoxyribonucleoside, ribonucleoside or ribonucleotide, and polymers thereof. Unless specifically limited, the terms cover nucleic acids containing known analogs of natural nucleotides, and the analogs have binding properties similar to reference nucleic acids and are metabolized in a manner similar to naturally occurring nucleotides. Unless otherwise limited specifically, the terms also mean oligonucleotide analogs, including PNAs (peptide nucleic acids) and DNA analogs used in antisense techniques (phosphorothioate, phosphoramidate, etc.). Unless otherwise specified, a particular nucleic acid sequence also implicitly encompasses its conserved modified variants (comprising, but not limited to, degenerate codon substitutions) and complementary sequences as well as explicitly specified sequences. Specifically, the degenerate codon substitution can be achieved by generating a sequence in which the 3rd position of one or more selected (or all) codons is replaced with a mixed base and/or a deoxyinosine residue (Batzer et al., *Nucleic Acid Res.,* 19:5081 (1991); Ohtsuka et al., *J. Biol. Chem.,* 260: 2605-2608 (1985); and Cassol et al., (1992); Rossolini et al., *Mol Cell. Probes,* 8:91-98 (1994)).

The terms "polypeptide" and "protein" are used interchangeably herein to mean polymers of amino acid residues. In other words, the description of a polypeptide is equally applicable to the description of a peptide and a protein, and vice versa. The terms apply to naturally occurring amino acid polymers, and amino acid polymers in which one or more amino acid residues are non-naturally encoded amino acids. As used herein, the terms encompass amino acid chains of any length, including full-length proteins (i.e., antigens), in which amino acid residues are linked via covalent peptide bonds.

The term "host cell" means a cell comprising the nucleotide of the present disclosure, regardless of the method used for insertion to produce a recombinant host cell, such as direct uptake, transduction, pairing, or other methods known in the art. An exogenous polynucleotide can exist as a non-integrated vector such as a plasmid, or can be integrated into the host's genome. Host cells may be prokaryotic cells or eukaryotic cells.

The term "transformation" means a process by which a heterologous DNA sequence is introduced into a host cell or organism.

The term "expression" means the transcription and/or translation of an endogenous gene or a transgene in a cell.

The term "scale-up" generally refers to the process of expanding the production of a device from a laboratory scale to an industrial scale. As used herein, this term includes the expansion of expression from a small-scale shake-flask to a small-scale fermenter or a fermenter with a larger volume.

Figure 3A:
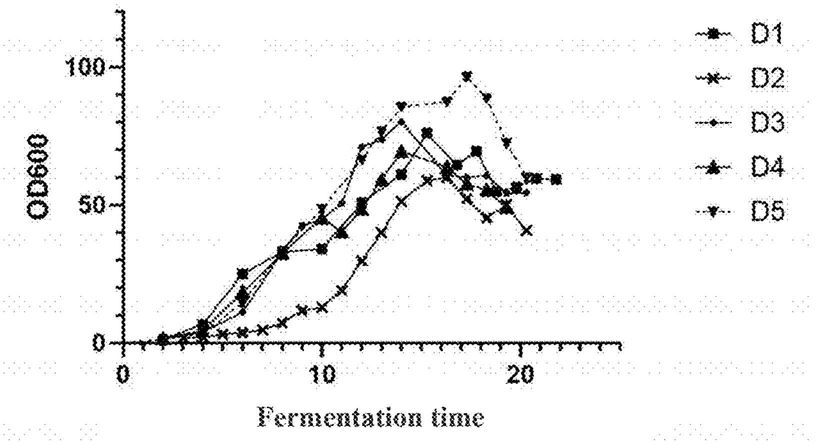
FIG. 3A shows $OD_{600}$ profile of the IdeE-1 expression strain during fermentation in a 5-L fermenter at different induction time points.
Figure 3B:
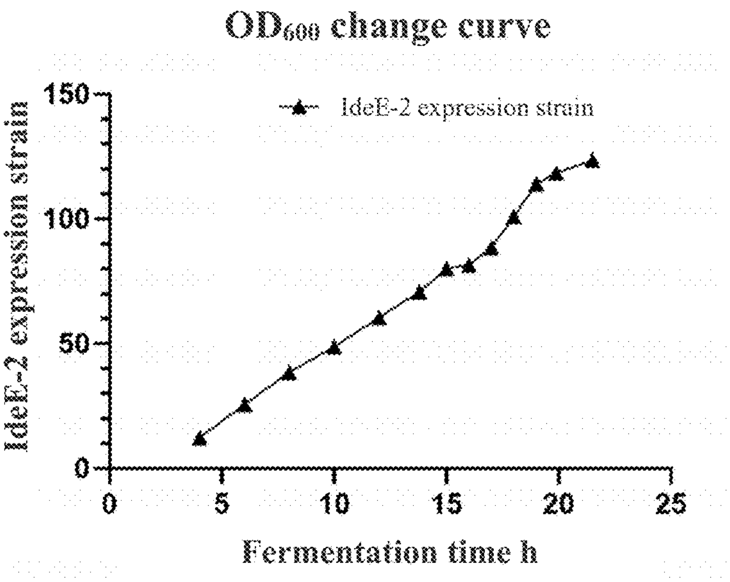
FIG. 3B shows $OD_{600}$ value of the IdeE-2 expression strain during fermentation in a 5-L fermenter at different induction time points.
Figure 3C:
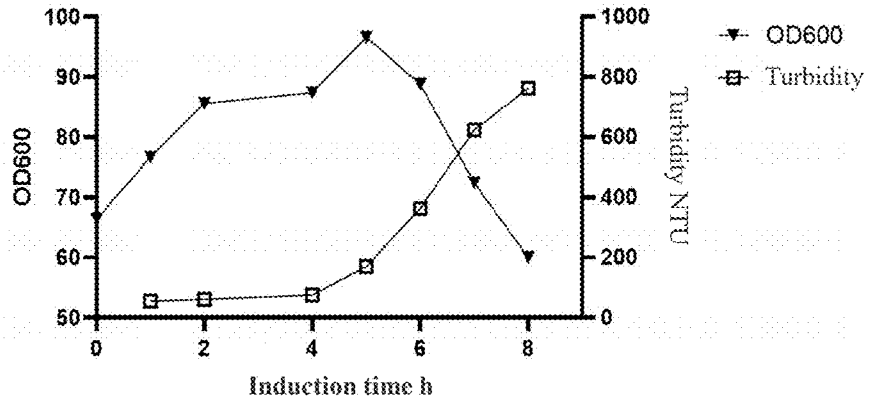
FIG. 3C shows the changes in $OD_{600}$ value and the fermentation supernatant turbidity of the IdeE-1 expression strain during fermentation in a 5-L fermenter at different induction time points.

The term "bacterial, fungal, or cellular autolysis" refers to the undesired lysis in a strain that occurs before a predetermined fermentation end point. Such undesired lysis often leads to a decrease in $OD_{600}$ value, increased viscosity or turbidity of the culture liquid, which in turn has an adverse effect on the expression level and product separation. Optionally, the "absence of bacterial, fungal, or cellular autolysis" described herein is characterized by the absence of at least 10%, at least 20%, at least 30%, at least 50%, at least 60%, at least 70%, at least 80%, at least 90%, or 100% decrease in $OD_{600}$ value at one or more sampling points after exceeding 40, 50, 60, 70, or 80 during 4 h, 8 h, 12 h, 16 h, 24 h, or longer following induced expression. A typical $OD_{600}$ value decrease is shown in FIG. 3A herein.

The advantageous effects of the present disclosure lie in the unexpected finding that the expression level of IdeE-1 is low, and the strain is unstable and prone to autolysis during the scale-up cultivation. Furthermore, the fermentation broth exhibits excessive viscosity, rendering solid-liquid separation ineffective and complicating downstream purification operations. In the present disclosure, provided is an immunoglobulin-degrading enzyme mutant IdeE-2 and an expression method thereof, which demonstrates improvements over IdeE-1 through: substantially enhanced expression levels, stable expression system performance, prevention of autolysis and viscosity increase of the fermentation broth during the scale-up cultivation, controllable final harvest volume through cell lysis, and facilitated subsequent purification procedures.

The present disclosure is further illustrated by the following examples, which are not intended to limit the present disclosure. Experimental procedures without specified conditions in the following examples were performed in accordance with conventional procedures and conditions, or in accordance with product instructions.

Example 1. Construction of IdeE-1 Expression Strain

A codon-optimized polynucleotide sequence encoding the IdeE-1 protein sequence (SEQ ID NO: 1) was synthesized. This sequence was engineered to incorporate an N-terminal signal peptide and a C-terminal 6× histidine tag. The synthesized construct was inserted into a pET32a expression vector, and a recombinant plasmid for expressing mutant IdeE was obtained after sequencing verification. The mutated recombinant plasmids were electroporated into *Escherichia coli* BL21 Star (DE3), and the transformed cells were plated on an LB agar plate containing 100 μg/mL ampicillin. The plate was cultured at 37° C. overnight until colonies grew out. A single colony was picked and inoculated into 3 mL of an LB medium containing 100 μg/mL ampicillin, and the mixture was cultured at 37° C. and 250 rpm overnight. 500 μL of the overnight bacterial culture was transferred to 50 mL of an LB medium containing 100 μg/mL ampicillin. After incubation at 37° C. for 4 h, 0.1 mM IPTG was added to induce expression, and the induced cultivation continued overnight. The bacterial culture after overnight induced culture was centrifuged to collect the culture supernatant. SDS-PAGE analysis was performed to determine a content of the mutant protein IdeE-1 in the supernatant, as shown in FIG. 1.

Example 2. Construction of IdeE-2 Expression Strain

Figure 2:
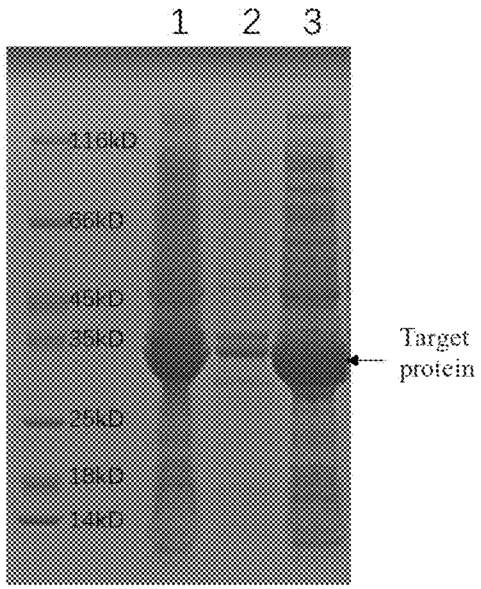
FIG. 2 shows the electrophoretic results of the expressed products in the fermentation bacterial cell lysate of the IdeE-2 expression strain.

A codon-optimized polynucleotide sequence encoding the IdeE-2 protein sequence (SEQ ID NO: 2) was synthesized. The synthesized sequence was inserted into a pET32a expression vector, and a recombinant plasmid for expressing mutant IdeE was obtained. The mutated recombinant plasmids were electroporated into *Escherichia coli* BL21 Star (DE3), and the transformed cells were plated on an LB agar plate containing 100 μg/mL ampicillin. The plate was cultured at 37° C. overnight until colonies grew out. A single colony was picked and inoculated into 3 mL of an LB medium containing 100 μg/mL ampicillin, and the mixture was cultured at 37° C. and 250 rpm overnight. 500 μL of the overnight bacterial culture was transferred to 50 mL of an LB medium containing 100 μg/mL ampicillin. After incubation at 37° C. for 4 h, 0.1 mM IPTG was added to induce expression, and the induced cultivation continued overnight. The bacterial culture after overnight induced cultivation was centrifuged to collect the bacterial cells, which were subjected to cell lysis using an ultrasonic disruptor. SDS-PAGE analysis was performed to determine the content of mutant protein IdeE-2 in both the cell debris pellet and lysate supernatant, as shown in FIG. 2.

Example 3. Culture of IdeE-1 and IdeE-2 Expression Strains in Fermenter

The secretory and intracellular expression strains constructed in Examples 1 and 2 were cultured in shake flasks, and gradually transferred to 5 L fermenters for fermentation culture, respectively. The fermentation culture was performed using fed-batch and deep aeration methods. Glycerol or glucose was selected as the limiting carbon source for pre-induction control of feeding, and IPTG and lactose were respectively selected as the inducer and the limiting carbon source for post-induction control of feeding. The fermentation was performed at 37° C., and pH was controlled at 6.0-7.2 by adding 25% ammonium hydroxide. The aeration rate of the fermenter was set to 0.5-2.0 vvm, and dissolved oxygen was maintained at about 30% by controlling the feeding rate, stirring speed, and aeration rate. During the fermentation culture, samples were periodically taken to measure $OD_{600}$ value, and when $OD_{600}$ value reached a predetermined value, IPTG/lactose feeding was initiated for induction. Fermentation was terminated after 8-16 h of induced culture. For the secretory expression strain, the $OD_{600}$ value decreased during the late induction phase, the bacterial culture gradually became viscous, and the turbidity significantly increased. After fermentation, the bacterial culture was too viscous to undergo effective solid-liquid separation by centrifugation, which was a typical *Escherichia coli* autolysis phenomenon. This phenomenon was confirmed through multiple experiments that the autolysis phenomenon during the late induction phase of this secretory expression strain was not accidental (FIG. 3A). The IdeE-2 expression strain exhibited continuously increasing $OD_{600}$ value during fermentation, with protein expression levels rising continuously throughout induction. Post-fermentation bacterial culture remained non-viscous, allowing efficient bacterial cell collection via centrifugation. These results demonstrated that secretory expression of the IdeE-1 mutant protein in *Escherichia coli* caused bacterial autolysis, precluding subsequent purification from the fermentation supernatant and impeding scale-up production.

Figure 4:
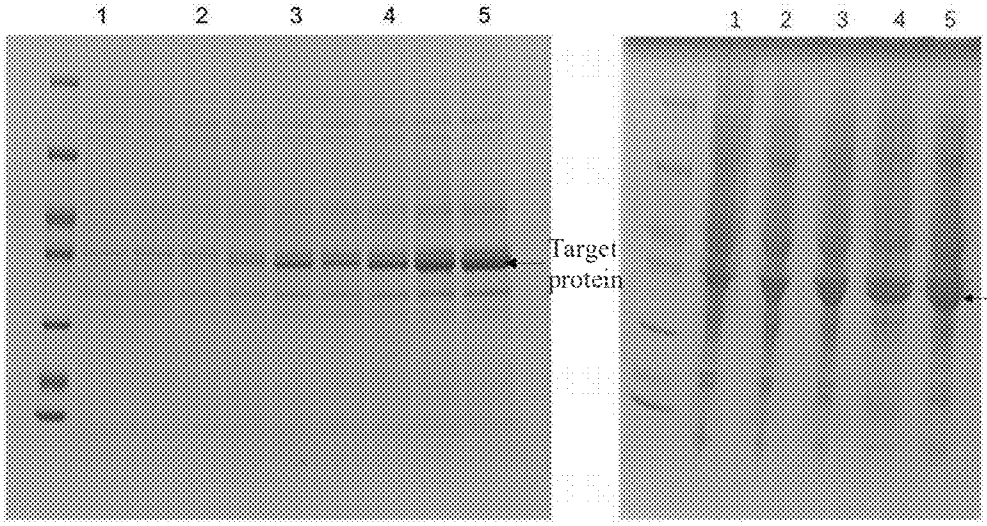
FIG. 4 shows the electrophoresis results of the expressed products of the IdeE-1 and IdeE-2 expression strains during fermentation in a 5-L fermenter at different induction time points.

As shown in FIG. 4, the expression level of IdeE-2 (the amino acid sequence is shown as SEQ ID NO: 2) was significantly higher than that of IdeE-1 (the amino acid sequence is shown as SEQ ID NO: 1). Furthermore, during the production process, the strain expressing protein IdeE-1 (SEQ ID NO: 1) exhibited greater instability, with bacterial cell autolysis phenomenon (FIG. 3A). Additionally, the viscosity of the fermentation broth of IdeE-1 expression increased, rendering solid-liquid separation ineffective. This led to a larger volume and higher difficulties for buffer exchange by ultrafiltration, thereby increasing purification difficulty.

| Sample | Amino acid sequence number | Expression level | Bacterial cell stability | Purification difficulty |
|---|---|---|---|---|
| IdeE-1 | SEQ ID NO: 1 | Low, 0.27 g/L | Low, prone to autolysis | Difficult, difficult solid-liquid separation and buffer exchange by ultrafiltration |
| IdeE-2 | SEQ ID NO: 2 | High, 5 g/L | High | Easy |

Example 4. In Vivo Efficacy Study

Figure 5:
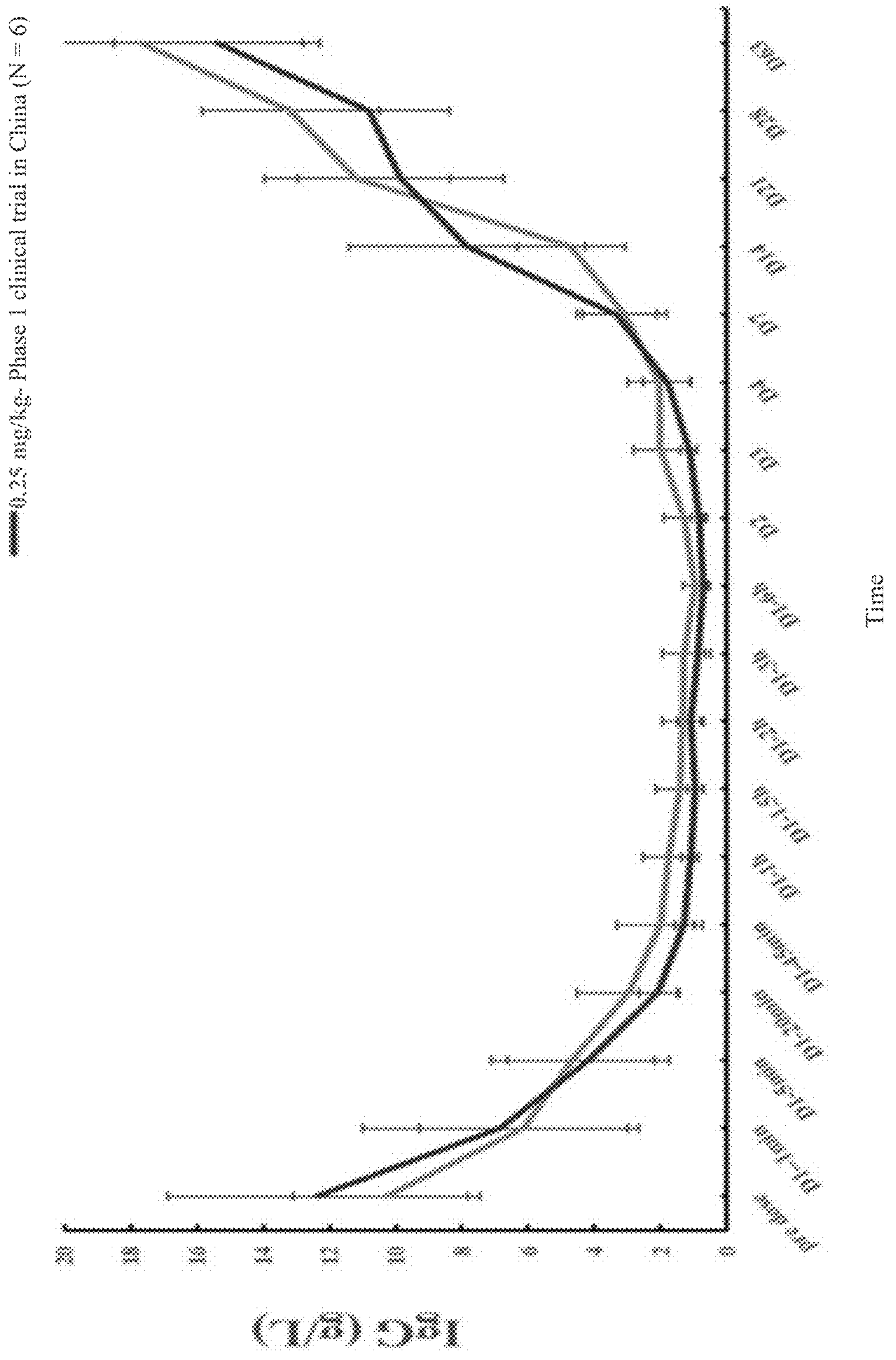
FIG. 5 shows the changes in the level of IgG degraded in vivo by KJ103 at a dose of 0.25 mg/kg.

The safety, tolerability, pharmacokinetic (PK) characteristics, pharmacodynamic characteristics, and immunogenicity of IdeE-2 (a novel low-immunogenicity immunoglobulin G-degrading enzyme) were evaluated in healthy Chinese and New Zealand subjects. A total of 68 healthy subjects were enrolled in the study, and all subjects completed the study. The results of Phase I clinical trials conducted in China and New Zealand were highly consistent, demonstrating that IdeE-2 exhibited good safety and tolerability in the healthy subjects. The PK curves of IdeE-2 across the dose groups demonstrated good reproducibility, with IdeE-2 exhibiting characteristics of rapid distribution and slow elimination in healthy subjects. The PK profile was consistent with the two-compartment model. Administration at the dose of 0.25 mg/kg was sufficient to achieve the optimal dose-response effect. IdeE-2 efficiently, rapidly, and specifically cleaved human IgG. At the dose of 0.25 mg/kg, IdeE-2 cleaved 95% IgG within 45 min to 6 h after administration, and a low IgG level (with an average decrease of not less than 70%) was maintained for one week (FIG. 5). The proportion and titer of pre-existing anti-IdeE-2 antibodies were low, demonstrating significant clinical advantages over the counterpart Imlifidase. The use of IdeE-2 enhanced clinical safety and efficacy. IdeE-2 is expected to provide a safer and more effective breakthrough therapy in: organ transplantation (both solid organ and hematopoietic stem cell transplantation), acute severe autoimmune diseases, and gene therapy applications.

The safety of IdeE-2 was superior to that of Imlifidase: The healthy subjects were given five escalating dose levels of IdeE-2 within a well-tolerated safety range, with safety and tolerability closely monitored.

The applicant declares that in the present disclosure, the examples above are used to describe the detailed method of the present disclosure, but the present disclosure is not limited to the detailed method above, that is, it does not mean that the present disclosure must rely on the detailed method above for implementation. It should be understood by those skilled in the art that any modifications of the present disclosure, equivalent substitutions of the raw materials of the product of the present disclosure, and the addition of auxiliary components, selection of specific modes, etc., are within the scope of protection and disclosure of the present disclosure.

```
Sequence
                                            SEQ ID NO: 1
TSVWTKGVTPLTPEQFRYNNEDVIHAPYLAHQGWYDITKAFDGKDNLLCG

AATAGNMLHWWFDQNKTEIEAYLSKHPDKQKIIFNNQELFDLKAAIDTKD

SQTNSQLFNYFRDKAFPNLSARQLGVMPDLVLDMFINGYYLNVFKTQSTD
```

-continued

VNRPYQDKDKRGGIFDAVFTRGDQTTLLTARHDLKNKGLNDISTIIKQEL

TEGRALALSHTYANVSISHVINLWGADENAEGNLEAIYVTDSDANASIGM

KKYFVGINAHGHVAISAKKIEGENIGAQVLGLFTLSSGKDIWQKLS

SEQ ID NO: 2

MITSVWTKGVTPLTPEQFRYNNEDVIHAPYLAHQGWYDITKAFDGKDNLL

CGAATAGNMLHWWFDQNKTEIEAYLSKHPDKQKIIFNNQELFDLKAAIDT

KDSQTNSQLFNYFRDKAFPNLSARQLGVMPDLVLDMFINGYYLNVFKTQS

TDVNRPYQDKDKRGGIFDAVFTRGDQTTLLTARHDLKNKGLNDISTIIKQ

ELTEGRALALSHTYANVSISHVINLWGADENAEGNLEAIYVTDSDANASI

GMKKYFVGINAHGHVAISAKKIEGENIGAQVLGLFTLSSGKDIWQKLS

SEQ ID NO: 3

ATGATCACCAGCGTGTGGACCAAAGGTGTTACCCCGCTGACCCCGGAGCA

GTTCCGTTACAACAACGAAGACGTTATTCACGCGCCGTACCTGGCGCACC

AAGGTTGGTATGATATCACCAAGGCGTTCGACGGCAAAGATAACCTGCTG

TGCGGTGCGGCGACCGCGGGTAACATGCTGCACTGGTGGTTTGACCAGAA

-continued

CAAGACCGAGATTGAAGCGTACCTGAGCAAACACCCGGATAAGCAGAAGA

TCATCTTCAACAACCAAGAACTGTTCGACCTGAAGGCGGCGATCGACACC

AAAGATAGCCAGACCAACAGCCAACTGTTCAACTATTTTCGTGATAAGGC

GTTTCCGAACCTGAGCGCGCGTCAGCTGGGTGTGATGCCGGACCTGGTTC

TGGATATGTTCATTAACGGCTACTATCTGAACGTGTTTAAAACCCAGAGC

ACCGATGTTAACCGTCCGTACCAAGACAAGGATAAACGTGGTGGCATCTT

CGACGCGGTGTTTACCCGTGGTGATCAGACCACCCTGCTGACCGCGCGTC

ACGACCTGAAGAACAAAGGTCTGAACGATATTAGCACCATCATTAAGCAA

GAACTGACCGAAGGTCGTGCGCTGGCGCTGAGCCACACCTATGCGAACGT

GAGCATCAGCCACGTTATTAACCTGTGGGGTGCGGACTTCAACGCGGAGG

GCAACCTGGAAGCGATCTACGTGACCGACAGCGATGCGAACGCGAGCATT

GGCATGAAGAAATATTTTGTGGGTATCAACGCGCACGGCCACGTTGCGAT

CAGCGCGAAGAAAATTGAGGGTGAAAACATCGGCGCGCAGGTTCTGGGTC

TGTTCACCCTGAGCAGCGGCAAGGATATTTGGCAAAAACTGAGCTAATGA

What is claimed is:

1. An immunoglobulin-degrading enzyme consisting of the amino acid sequence set forth in SEQ ID NO: 2.

2. The immunoglobulin-degrading enzyme according to claim 1, wherein the immunoglobulin-degrading enzyme does not cause bacterial autolysis during expression.

3. The immunoglobulin-degrading enzyme according to claim 2, wherein, during expression in a bacterial host, the $OD_{600}$ value of the bacterial host does not decrease after exceeding 40, 50, 60, 70, or 80.

4. The immunoglobulin-degrading enzyme according to claim 3, wherein, during expression in a bacterial host, the $OD_{600}$ value does not decrease after exceeding 70.

5. The immunoglobulin-degrading enzyme according to claim 3, wherein, during expression in a bacterial host, the $OD_{600}$ value does not decrease after exceeding 80.

6. A nucleotide sequence encoding the immunoglobulin-degrading enzyme according to claim 1, comprising:

(a) a nucleotide sequence set forth in SEQ ID NO: 3;

(b) a nucleotide sequence having at least 85%, at least 90%, at least 95%, at least 96%, at least 97%, at least 98%, or at least 99% but less than 100% sequence homology to the nucleotide sequence set forth in SEQ ID NO: 3; or (c) a nucleotide sequence having one or more nucleotide substitutions, additions, and/or deletions compared with SEQ ID NO: 3.

7. An expression vector, comprising the nucleotide sequence according to claim 6.

8. A host cell, comprising the nucleotide sequence according to claim 6.

9. The host cell according to claim 8, wherein the host cell is a bacterial cell.

10. The host cell according to claim 9, wherein the bacterial cell is an *Escherichia coli Escherichia coli* cell.

11. A method for intracellular expression of an immunoglobulin-degrading enzyme, comprising the following steps: (a) selecting a single colony of a host cell; (b) culturing a seed culture; (c) culturing the seed culture in a fermenter; (d) inducing expression of the immunoglobulin-degrading enzyme; and (e) collecting the expressed immunoglobulin-degrading enzyme;

wherein the host cell comprises a nucleotide sequence encoding the immunoglobulin-degrading enzyme or an expression vector comprising a nucleotide sequence encoding the immunoglobulin-degrading enzyme;

wherein the immunoglobulin-degrading enzyme consists of the amino acid sequence as set forth in SEQ ID NO:2;

wherein the host cell is a bacteria cell and does not autolyze during expression;

and wherein the immunoglobulin-degrading enzyme is collected by centrifugation to collect the bacterial cells followed by cell lysis and purification of the enzyme from the lysate.

12. A composition, comprising: the immunoglobulin-degrading enzyme according to claim 1; and optionally a pharmaceutically acceptable carrier or excipient.

13. The composition according to claim 12, further comprising: an antibody or a protein comprising an Fc fragment, wherein a target of the antibody is selected from the following group: a cell surface protein, a cytokine, a hormone, an enzyme, an intracellular messenger, an intercellular messenger, and an immune checkpoint inhibitor.

14. The composition according to claim 12, further comprising: a viral vector drug and/or a drug capable of reducing a blood IgG level.

15. The composition according to claim 14, wherein the viral vector drug is selected from the following group: an oncolytic virus, a gene therapy virus, and a viral vector vaccine; and/or the drug capable of reducing the blood IgG level is selected from the following group: an FcRn antibody and an Fc fragment variant with high affinity for FcRn.

16. A kit, comprising:

(1) the immunoglobulin-degrading enzyme according to claim 1; and (2) one or more selected from the following group: (a) a pharmaceutically acceptable carrier or excipient; (b) an antibody or a protein comprising an Fc fragment; and/or (3) a viral vector drug selected from an oncolytic virus, a gene therapy virus, and a viral vector vaccine; and/or (4) a drug capable of reducing a blood IgG level selected from an FcRn antibody and an Fc fragment variant with high affinity for FcRn.

17. A kit, comprising a first kit and a second kit, wherein, the first kit comprises the immunoglobulin-degrading enzyme according to claim 1, and the second kit comprises one or more selected from the following group:

(1) a pharmaceutically acceptable carrier or excipient; (2) an antibody or a protein comprising Fc; and/or (3) a viral vector drug; and/or (4) a drug capable of reducing a blood IgG level, wherein the viral vector drug is selected from an oncolytic virus, a gene therapy virus, and a viral vector vaccine; the drug capable of reducing the blood IgG level is selected from an FcRn antibody and an Fc fragment variant with high affinity for FcRn.

18. A nucleotide sequence encoding the immunoglobulin-degrading enzyme according to claim 1.

19. The immunoglobulin-degrading enzyme according to claim 1, wherein the immunoglobulin-degrading enzyme is intracellularly expressed.

* * * * *